United States Patent
Matsuo et al.

(10) Patent No.: US 7,920,733 B2
(45) Date of Patent: Apr. 5, 2011

(54) BIOCHEMICAL EXAMINATION APPARATUS AND BIOCHEMICAL EXAMINATION METHOD

(75) Inventors: Yuichiro Matsuo, Hachioji (JP); Takami Shibazaki, Hachioji (JP); Yuko Saida, Hachioji (JP)

(73) Assignee: Olympus Corporation, Tokyo (JP)

(*) Notice: Subject to any disclaimer, the term of this patent is extended or adjusted under 35 U.S.C. 154(b) by 924 days.

(21) Appl. No.: 11/880,657

(22) Filed: Jul. 23, 2007

(65) Prior Publication Data

US 2008/0018778 A1 Jan. 24, 2008

Related U.S. Application Data

(63) Continuation of application No. PCT/JP2006/301050, filed on Jan. 24, 2006.

(30) Foreign Application Priority Data

Jan. 24, 2005 (JP) .................................. 2005-015546

(51) Int. Cl.
*G06K 9/00* (2006.01)
*G03B 7/00* (2006.01)

(52) U.S. Cl. ........................................ 382/129; 348/362

(58) Field of Classification Search .......... 382/128–134, 382/100; 348/61–80, 131–135, 362–365, 348/370; 250/216, 234–235, 227.11, 201.3, 250/201–4, 306–307, 23; 359/363–376, 359/385–389, 236–237, 850–851; 435/6, 435/7.1, 287.2, 288.7; 396/20, 24, 116

See application file for complete search history.

(56) References Cited

U.S. PATENT DOCUMENTS

| | | | |
|---|---|---|---|
| 6,191,885 B1 | 2/2001 | Kitagawa | |
| 6,400,487 B1* | 6/2002 | Harris et al. | 359/210.1 |
| 6,791,618 B1 | 9/2004 | Shimizu | |
| 7,499,806 B2* | 3/2009 | Kermani et al. | 702/19 |
| 2005/0036667 A1* | 2/2005 | So et al. | 382/128 |
| 2008/0277595 A1* | 11/2008 | Lundquist et al. | 250/458.1 |
| 2010/0167413 A1* | 7/2010 | Lundquist et al. | 436/172 |

FOREIGN PATENT DOCUMENTS

| | | |
|---|---|---|
| JP | 2000-98259 | 4/2000 |
| JP | 2000-180361 | 6/2000 |
| JP | 2002-350446 | 12/2002 |
| JP | 2003-227799 | 8/2003 |
| JP | 2003-524754 | 8/2003 |
| JP | 2004-28775 | 1/2004 |
| JP | 2004101354 | 4/2004 |
| JP | 2005-214924 | 8/2005 |

\* cited by examiner

*Primary Examiner* — Samir A Ahmed
*Assistant Examiner* — Mehdi Rashidian
(74) *Attorney, Agent, or Firm* — Scully, Scott, Murphy & Presser, P.C.

(57) ABSTRACT

First, image capturing is performed in the exposure time of ExpStart. If the maximum intensity value of all the pixels of an image is smaller than TransStart, the exposure time is increased and the image capturing is performed again. After that, increase in the exposure time and the image capturing are repeatedly performed until the maximum intensity value of all the pixels of the captured optical image becomes equal to or greater than TransStart. When the maximum intensity value becomes equal to or greater than TransStart, image data is transferred to a computer to be recorded on the hard disk, and the number of images recorded is counted. Subsequently, the increase in the exposure time, the image capturing, transfer and record of the image data, and count of the number of images recorded are repeatedly performed. The image capturing is finished when the minimum intensity value in an area of the fluorescent image that is smaller than the entire area becomes larger than TransEnd, the number of images recorded becomes larger than TransPicts, or the exposure time becomes longer than MaxExpTime.

4 Claims, 9 Drawing Sheets

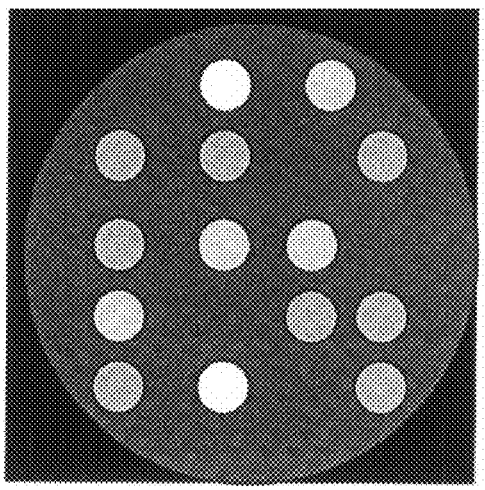
F I G. 5D
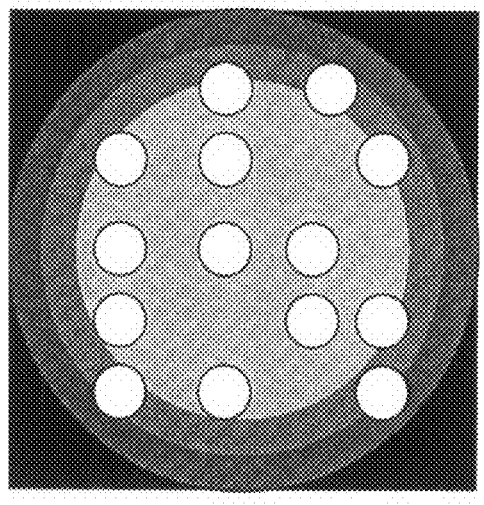
F I G. 5E

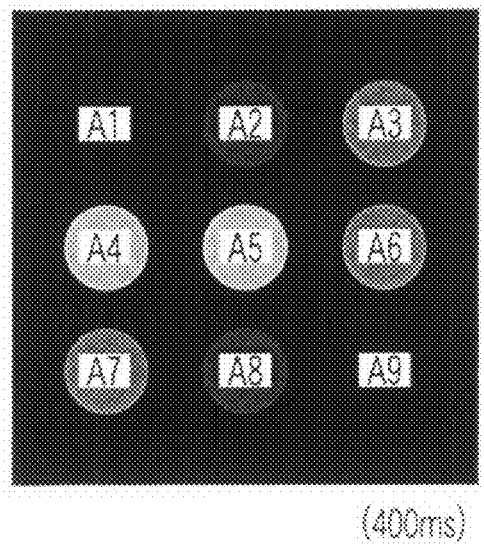
F I G. 8A
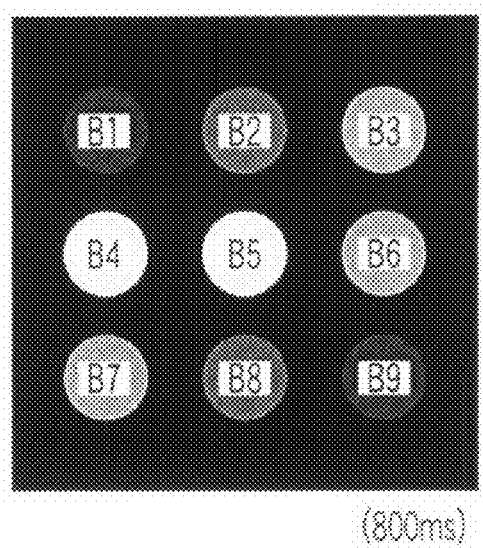
F I G. 8B

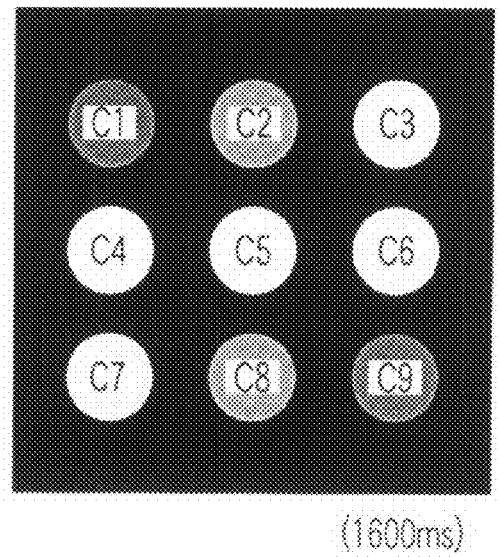
F I G. 8C
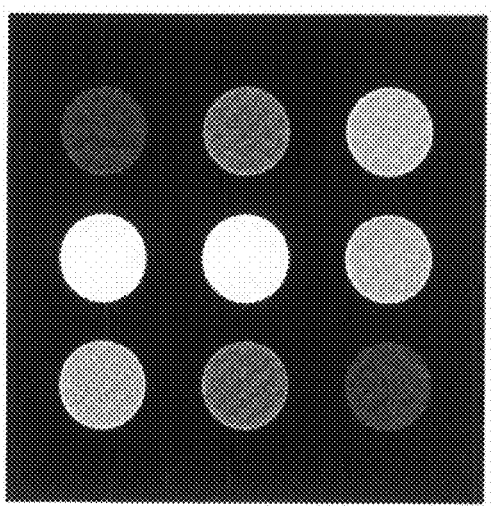
F I G. 8D

BIOCHEMICAL EXAMINATION APPARATUS AND BIOCHEMICAL EXAMINATION METHOD

CROSS-REFERENCE TO RELATED APPLICATIONS

This is a Continuation Application of PCT application No. PCT/JP2006/301050, filed Jan. 24, 2006, which was published under PCT Article 21(2) in Japanese.

This application is based upon and claims the benefit of priority from prior Japanese Patent Application No. 2005-015546, filed Jan. 24, 2005, the entire contents of which are incorporated herein by reference.

BACKGROUND OF THE INVENTION

1. Field of the Invention

The present invention relates to an apparatus and method for analyzing a biochemical reaction.

2. Description of the Related Art

Analysis has recently been performed on the genes of many creatures including human beings and many plants including rice. In the recent years, there has been developed an examination method using a DNA chip or a DNA microarray having DNAs regularly arrayed on a semiconductor or the like. This examination method can simultaneously examine a plurality of genes. This examination method is introduced as a conventional technique that uses a three-dimensional array and detects it in Jpn. Pat. Appln. KOKAI Publication No. 2002-350446. This reference discloses a biochemical examination method that can simultaneously detect light intensities corresponding to the respective probe array elements with a practically large dynamic range by using an area sensor or a line sensor having a general dynamic range.

Jpn. Pat. Appln. KOKAI Publication No. 2002-350446 discloses a method of allowing an examiner to switch ND filters and place a desired ND filter on an observation optical path as one of the biochemical examination methods that can simultaneously detect the light intensities corresponding to the respective probe array elements with the practically large dynamic range by using the area sensor or the line sensor having the general dynamic range.

Jpn. Pat. Appln. KOKAI Publication No. 2002-350446 also discloses a method of changing the light requirement of fluorescence by changing the accumulation time of the CCD in a CCD camera as another biochemical examination method. For example, this method sequentially increases the accumulation time (t0, 2t0, 4t0, ..., $2^{n-1}$t0 (n=1, 2, ...)) at a predetermined ratio, captures fluorescent images of the biochemical examination array, and sends each fluorescent image as a target image to an image processing unit immediately before the CCD is saturated.

In addition, with regard to a method of determining the maximum accumulation time of a CCD, Jpn. Pat. Appln. KOKAI Publication No. 2002-350446 discloses a method of determining the maximum value of the accumulation time in accordance with the condition that the light requirement of light corresponding to the minimum emission intensity of array element areas in a biochemical examination array falls within the linear area of the output characteristics of an array type detector.

BRIEF SUMMARY OF THE INVENTION

According to an aspect, the present invention is directed to a biochemical examination apparatus for measuring fluorescence emitted from a biochemical examination array to analyze a biochemical reaction. A biochemical examination apparatus according to the present invention comprises illumination means for applying exciting light to a biochemical examination array, capturing means for capturing an optical image emitted from the biochemical examination array, and recording means for saving the captured optical image, wherein the capturing means repeatedly captures an optical image while gradually prolonging an exposure time from an initial value defined by a first parameter, and the recording means starts recording the optical image when a maximum intensity of all pixels of the captured optical image becomes equal to or greater than an intensity defined by a second parameter, and finishes recording the optical image when a minimum intensity of pixels in an area smaller than an entire area of the captured optical image becomes greater than an intensity defined by a third parameter.

According to another aspect, the present invention is directed to a biochemical examination method for measuring fluorescence emitted from a biochemical examination array to analyze a biochemical reaction. A biochemical examination method according to the present invention comprises applying exciting light to the biochemical examination array, repeatedly capturing an optical image emitted from the biochemical examination array in response to application of the exciting light while gradually prolonging an exposure time from an initial value defined by a first parameter, and starting recording the optical image when a maximum intensity of all pixels of the captured optical image becomes equal to or greater than an intensity defined by a second parameter during repetitive image capturing, and finishing recording the optical image when a minimum intensity of pixels in an area smaller than an entire area of the captured optical image becomes greater than an intensity defined by a third parameter.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5D shows an image captured in a prolonged exposure time after capturing of the image shown in FIG. 5C;

FIG. 5E shows an image captured in a prolonged exposure time after capturing of the image shown in FIG. 5D;

FIG. 8A shows a fluorescent image of a biochemical examination array 100 captured in an exposure time of 400 ms;

FIG. 8B shows a fluorescent image of the biochemical examination array 100 captured in an exposure time of 800 ms;

FIG. 8C shows a fluorescent image of the biochemical examination array 100 captured in an exposure time of 1,600 ms; and FIG. 8D shows a hybrid image formed on the basis of the images shown in FIGS. 8A, 8B, and 8C.

DETAILED DESCRIPTION OF THE INVENTION

An embodiment of the present invention will be described below with reference to the views of the accompanying drawing.

Figure 1:
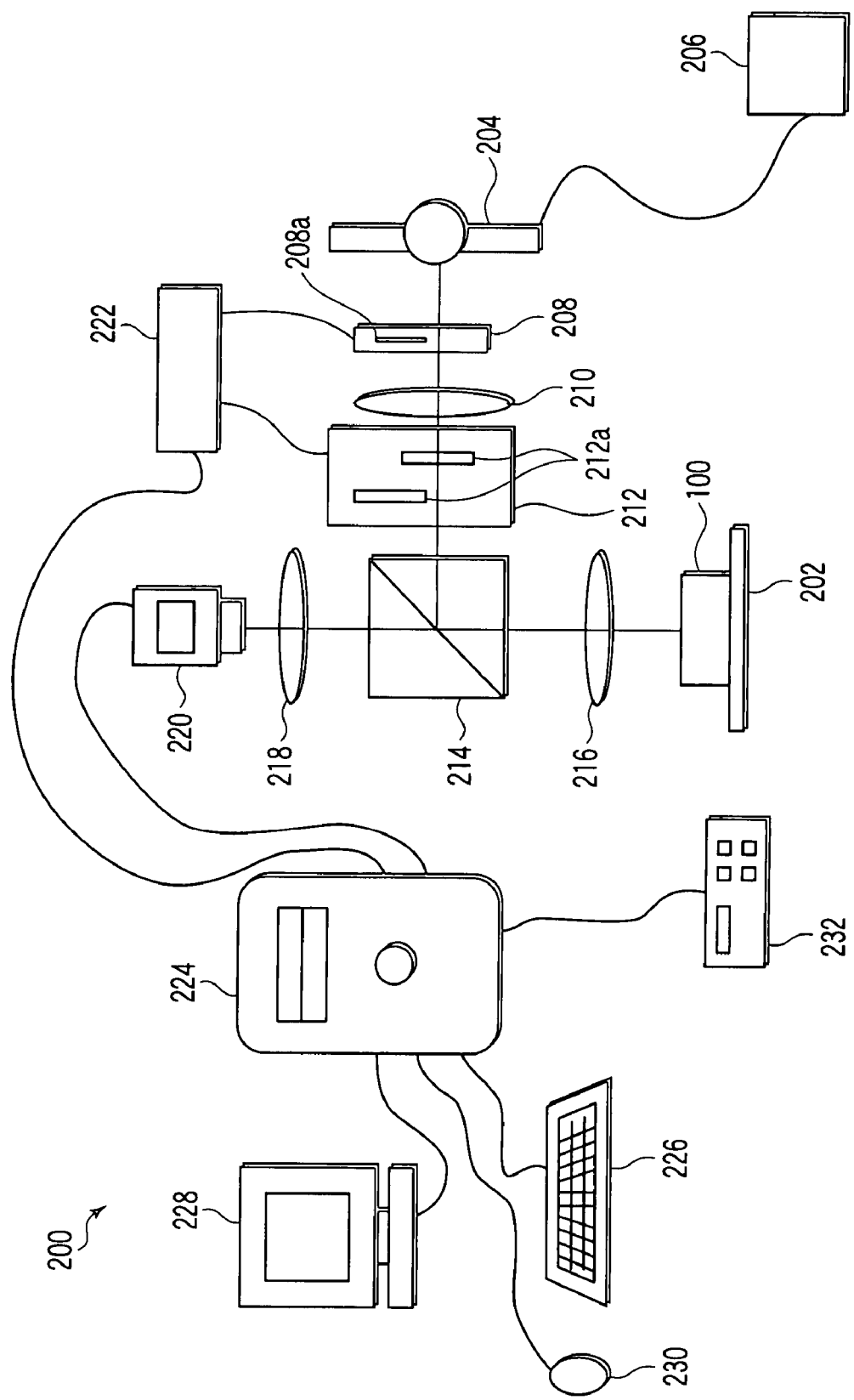
FIG. 1 shows the arrangement of a biochemical examination apparatus according to an embodiment of the present invention.

FIG. 1 shows the arrangement of a biochemical examination apparatus according to an embodiment of the present invention. Referring to FIG. 1, an exciting light source 204 comprises one of various kinds of lamps such as a mercury light source, an LED, or the like and is connected to a power supply unit 206. A shutter unit 208 incorporating a shutter plate 208a, a lens 210, a filter unit 212 incorporating two exciting filters 212a, and a dichroic mirror 214 are arranged on the optical path of exciting light emitted from the exciting light source 204. An objective lens 216 and a stage 202 on which a biochemical examination array 100 is mounted are arranged on the reflection optical path of the dichroic mirror 214. An image formation lens 218 and a CCD camera 220 as an imager are arranged on the transmission optical path of the dichroic mirror 214. The CCD camera 220 incorporates a buffer memory (not shown) that can temporarily store at least one captured image and a signal processor (not shown) that can perform image computing such as signal intensity detection with respect to an image in the buffer memory. A computer 224 can control the shutter unit 208 and the filter unit 212 through a universal control box 222. The stage 202, which can be motor-driven to be positioned in the X and Y directions, can be controlled by the computer 224 through a stage controller 232. A keyboard 226, monitor 228, and mouse 230 are connected to the computer 224.

In other words, a biochemical examination apparatus 200 comprises the stage 202 on which the biochemical examination array 100 is placed, the exciting light source 204 that emits exciting light, the dichroic mirror 214 that reflects exciting light toward the biochemical examination array 100 and transmits fluorescence generated from the biochemical examination array 100, and the CCD camera 220 for capturing a fluorescent image of the biochemical examination array 100. A fluorescent image is a kind of optical image. Optical images are images based on various kinds of light as signals, which include fluorescence, phosphorescence, chemiluminescence, bioluminescence, scattered light, and reflected light.

The biochemical examination apparatus 200 further comprises the shutter unit 208 for shutting off exciting light as needed, the lens 210, and the filter unit 212 for selecting the wavelength of exciting light. The shutter unit 208, lens 210, and filter unit 212 are sequentially arranged on an optical path from the exciting light source 204 to the dichroic mirror 214.

The biochemical examination apparatus 200 comprises the objective lens 216 placed between the dichroic mirror 214 and the stage 202 and the image formation lens 218 placed between the dichroic mirror 214 and the CCD camera 220.

In the optical system having this arrangement, the exciting light source 204, shutter unit 208, lens 210, filter unit 212, dichroic mirror 214, and objective lens 216 constitute illumination means for applying exciting light to the biochemical examination array 100. The objective lens 216, image formation lens 218, and CCD camera 220 constitute capturing means for capturing an optical image emitted from the biochemical examination array 100.

The biochemical examination apparatus 200 further comprises the power supply unit 206 for driving the exciting light source 204, the stage controller 232 for driving the stage 202, and the universal control box 222 for driving the shutter unit 208 and the filter unit 212.

The biochemical examination apparatus 200 comprises the computer 224 that controls the CCD camera 220, stage controller 232, and universal control box 222. The keyboard 226, monitor 228, and mouse 230, which constitute a user interface, are connected to the computer 224. The computer 224 incorporates a hard disk and constitutes recording means for saving the captured optical image.

Figure 2:
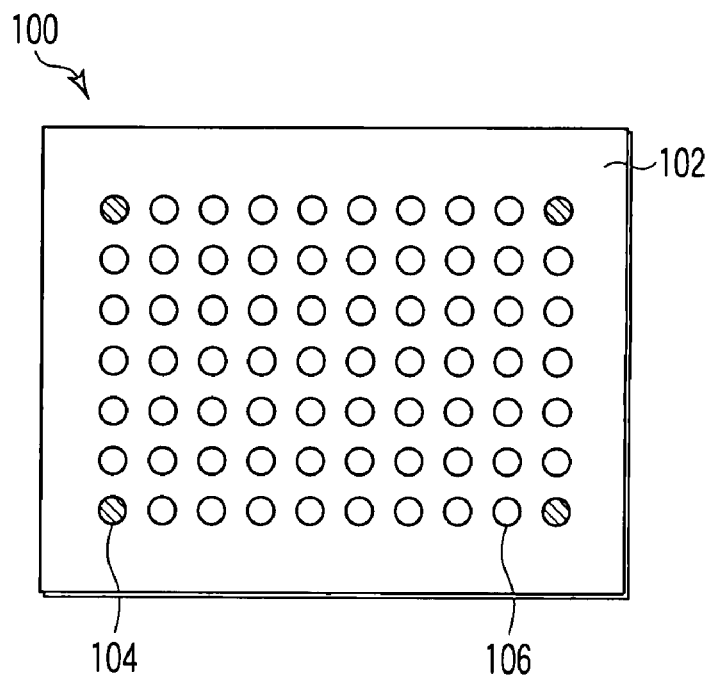
FIG. 2 is a plan view of a biochemical examination array to be examined by the biochemical examination apparatus shown in FIG. 1.
Figure 3:
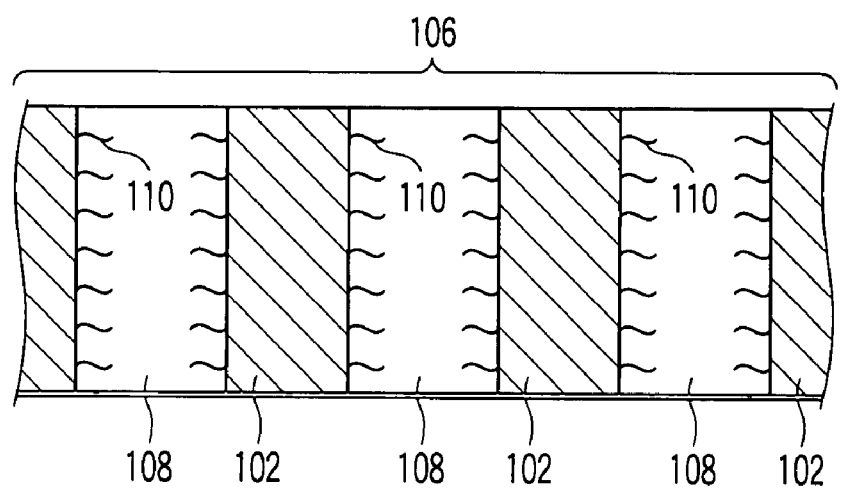
FIG. 3 is a cross-sectional view of array elements of the biochemical examination array shown in FIG. 2.

FIGS. 2 and 3 show a biochemical examination array to be examined by the biochemical examination apparatus shown in FIG. 1. The biochemical examination array 100, which is a three-dimensional array, includes a porous three-dimensional base material 102 and many probe array elements (probe spots) 106 formed in the three-dimensional base material 102, as shown in FIG. 2. The probe array elements 106 are two-dimensionally arrayed on the three-dimensional base material 102. Position detection array elements (position detection spots) 104 are formed in the four corners of the array area of the probe array elements 106. The three-dimensional base material 102 has many through holes. As shown in FIG. 3, probes 110 that react with specific substances are solid-phased on the inner walls of through holes 108 located in the probe array elements 106. The probe array elements (probe spots) 106 are formed by, for example, dispensing a necessary amount of solution containing probes on the three-dimensional base material 102.

The plurality of probe array elements 106 on the three-dimensional base material 102 include a plurality of types of elements. Each probe array element 106 contains probes 110 of the same type. When reacting with a specific substance, the probe 110 emits specific fluorescence upon application of specific exciting light.

The biochemical examination apparatus 200 is controlled by a control program operating on the computer 224. In other words, the computer 224 includes a control program for controlling the overall biochemical examination apparatus 200. This control program reads out parameters for its operation and the operation of each unit from an initial data file like that shown in FIG. 4 to control the overall biochemical examination apparatus 200.

Figure 4:
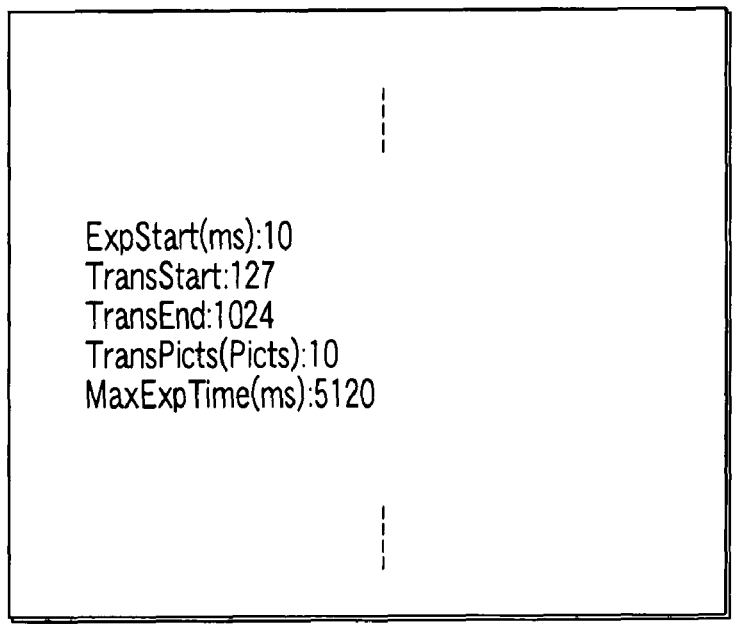
FIG. 4 shows part of an initial data file read by a control program operating on the computer shown in FIG. 1.

FIG. 4 shows an extracted part of the initial data file. The examiner or the manager of the apparatus can easily modify and change this initial data file by using a general editor or the like. That is, the examiner or the manager of the apparatus can easily modify and change the initial data file by operating the keyboard 226 while watching the monitor 228 and also operating the mouse 230 as needed. The initial data file contains various parameters. The monitor 228, keyboard 226, and mouse 230 constitute input means for allowing arbitrarily setting parameters in the initial data file.

The parameters shown in FIG. 4 are capturing parameters to be set when the CCD camera 220 captures fluorescent images of the biochemical examination array 100.

ExpStart is the initial value of an exposure time (the electric charge accumulation time of the CCD) to be set when the CCD camera 220 captures fluorescent images of the biochemical examination array 100. When the examiner issues an instruction to start capturing fluorescent images of the biochemical examination array 100, the CCD camera 220 repeatedly captures the biochemical examination array 100 while changing the exposure time so as to gradually increase it from the initial value. Although not limited to this, the exposure time is changed at a rate of, for example, $10 \times 2^{n-1}$ (n=1, 2, ...) [ms].

TransStart is a reference value for a pixel intensity value by which the CCD camera 220 determines whether to start recording (saving) a fluorescent image. That is, when, of pixels in an area near the center that is smaller than the entire area of a captured fluorescent image of the biochemical examination array 100, the intensity value of a pixel that is the brightest becomes equal to or greater than the value of TransStart, the CCD camera 220 starts transferring the image data to the computer 224. In response to this operation, the storage device (the hard disk in the computer 224) starts recording (saving) the image data.

TransEnd is a reference value for a pixel intensity value by which the CCD camera 220 determines whether to finish recording (saving) a fluorescent image. That is, when, of all the pixels of a captured fluorescent image of the biochemical examination array 100, the intensity value of a pixel that is the darkest becomes larger than the value of TransEnd, the CCD camera 220 finishes transferring image data to the computer 224. In response to this operation, the storage device (the hard disk in the computer 224) finishes recording (saving) image data.

TransPicts is a reference value for the number of images recorded (saved) by which the CCD camera 220 determines whether to finish recording (saving) a fluorescent image. That is, when the number of fluorescent images of the biochemical examination array transferred to the computer 224 becomes larger than the value of TransPicts, the CCD camera 220 finishes transferring image data to the computer 224. In response to this operation, the storage device (the hard disk in the computer 224) finishes recording (saving) image data.

MaxExpTime is a reference value for an exposure time by which the CCD camera 220 determines whether to finish recording (saving) a fluorescent image. That is, when the exposure time in which a fluorescent image of the biochemical examination array 100 is captured becomes larger than the value of MaxExpTime, the CCD camera 220 finishes transferring image data to the computer 224. In response to this operation, the storage device (the hard disk in the computer 224) finishes recording (saving) image data.

The operation of the biochemical examination apparatus 200 will be described next.

The examiner generates a solution containing two kinds of biochemical substances labeled with, for example, two-color fluorescent molecules (or chemiluminescent molecules) as preparation for biochemical examination. In this case, the examiner generates two kinds of biochemical substance solutions that the examiner wants to compare at the same concentration. One solution is labeled with FITC, and the other solution is labeled with rhodamine. These labeling substances may be other kinds of substances as long as they have different fluorescence wavelengths. Subsequently, the examiner mixes and agitates the two kinds of biochemical substances, which the examiner generated, at a volume ratio of 1:1. The mixing ratio may be changed in accordance with the characteristics of the two kinds of biochemical substance solutions and labeling substances.

The examiner supplies the mixture of the biochemical substances to the biochemical examination array 100 to make it specifically react with probes. In this case, the examiner places the biochemical examination array 100 on the stage 202 under the observation of the biochemical examination apparatus 200 shown in FIG. 1, and uniformly supplies the mixture of the biochemical substances to the surface of the array. With this operation, specific binding reactions occur between the probes in the probe array elements 106 on the biochemical examination array 100 and the solution mixture. As a result, a quantity of fluorescent molecules (or chemiluminescent molecules) corresponding to the intensity of a reaction indirectly bind to the probe in each probe array element 106.

The examiner removes unreacted biochemical substances from the biochemical examination array 100. In this case, the examiner removes unreacted biochemical substances from each probe array element 106 of the biochemical examination array 100 after the above binding reactions. In general, a cleaning method using a cleaning fluid is used. If the reaction carrier has a solid structure, unreacted biochemical substances may be removed together with the solution by using a pump instead of a cleaning fluid. Obviously, however, using a cleaning fluid removes unreacted biochemical substances more reliably.

The examiner operates the computer 224 through the monitor 228 in order to capture a fluorescent image of the biochemical examination array 100 for each labeling substance by using the CCD camera 220. When the examiner clicks the "capture" button displayed on the monitor 228 with the mouse 230, the computer 224 transmits a command to the universal control box 222 to place an exciting filter corresponding to a desired fluorescent molecule color on the illumination optical path by switching the two exciting filters 212a incorporated in the filter unit 212. The computer 224 transmits a command to open the shutter plate 208a incorporated in the shutter unit 208 in the universal control box 222. Exciting light from the exciting light source 204 passes through the lens 210 and the exciting filter 212a, is reflected by the dichroic mirror 214, and is applied to the entire upper surface of the biochemical examination array 100 through the objective lens 216. As a result, the fluorescence generated by fluorescent molecules in each probe array element 106 passes through the objective lens 216, dichroic mirror 214, and image formation lens 218 and is guided to the CCD camera 220.

The CCD camera 220 repeatedly performs image capturing while gradually prolonging the exposure time (accumulation time) from the initial value indicated by ExpStart written in the initial data file. In this embodiment, ExpStart is 10 ms, and the exposure time (accumulation time) is increased at a rate of $10 \times 2^{n-1}$ (n=1, 2, ...) ms. Every time image capturing is complete, it is determined by scanning whether the maximum value of the intensities of all the pixels of a captured fluorescent image is equal to or greater than the pixel intensity indicated by TransStart written in the initial data file.

Figure 5A:
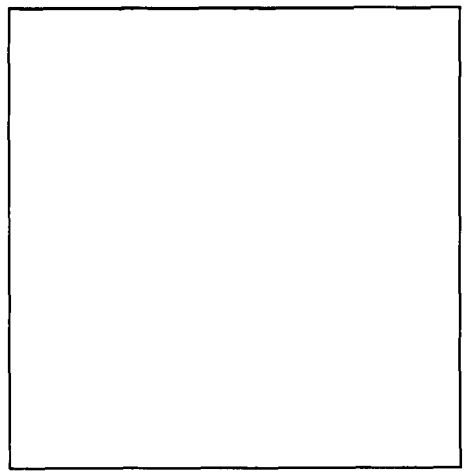
FIG. 5A shows an image captured immediately after the start of image capturing.

The CCD camera 220 transfers no image data to the computer 224 while the maximum intensity value of all the pixels of an image is smaller than TransStart. FIG. 5A shows an image captured immediately after the start of image capturing. That is, this is the image captured in an exposure time of 10 ms. The maximum value of the intensity values of all the pixels of the image in FIG. 5A is smaller than TransStart. For this reason, the CCD camera 220 does not transfer the image data in FIG. 5A to the computer 224. The CCD camera 220 repeats the same operation until the maximum intensity value of all the pixels of an image becomes equal to or greater than TransStart.

Figure 5B:
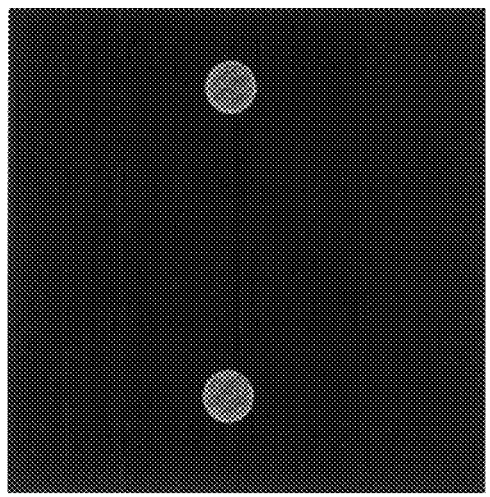
FIG. 5B shows an image immediately after the maximum intensity value of all the pixels of an image becomes equal to or greater than TransStart.

When the maximum intensity value of all the pixels of an image becomes equal to or greater than TransStart, the CCD camera 220 starts transferring the image data to the computer 224. FIG. 5B shows an image immediately after the maximum intensity value of all the pixels of an image becomes equal to or greater than TransStart. The maximum intensity value of all the pixels of the image in FIG. 5B is equal to or greater than TransStart, and two probe array elements appear. For this reason, the CCD camera 220 transfers the image data in FIG. 5B to the computer 224. The transferred image data is recorded (saved) on the hard disk in the computer 224.

Figure 5C:
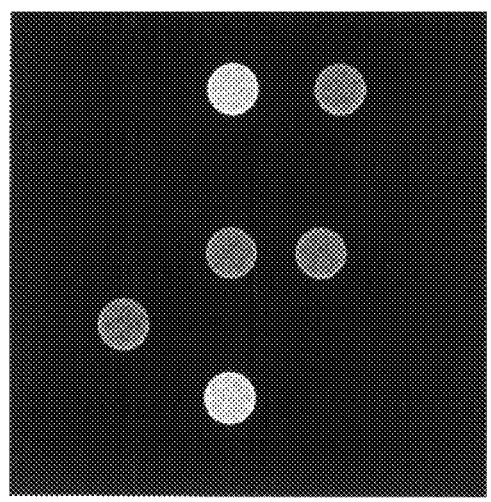
FIG. 5C shows an image captured in a prolonged exposure time after capturing of the image shown in FIG. 5B.
Figure 5F:
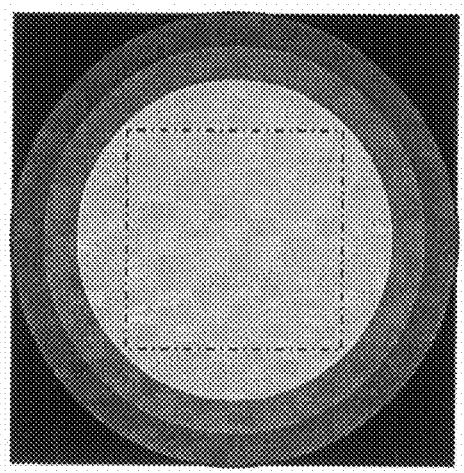
FIG. 5F shows an area of a fluorescent image that is smaller than the entire area and in which the minimum intensity value to be compared with TransEnd is checked.

The CCD camera 220 keeps transferring image data to the computer 224 while the minimum intensity value in an area near the center of a fluorescent image that is smaller than the entire area is equal to or less than TransEnd. As the exposure time prolongs, more probe array elements gradually appear in a fluorescent image of the biochemical examination array 100 as shown in FIGS. 5C, 5D, and 5E.

If the minimum intensity value in an area of a fluorescent image that is smaller than the entire area becomes larger than TransEnd, the CCD camera 220 finishes transferring the image data to the computer 224. This terminates recording (saving) of image data on the hard disk in the computer 224.

In this case, image data may be temporarily sent to the computer and determined whether to save the image data. This eliminates the necessity to use any signal processor for image computing in the CCD camera.

More preferably, while image data is transferred to the computer 224, a fluorescent image of the biochemical examination array 100 is captured with no illumination light being applied in each exposure time, i.e., the shutter unit 208 being closed, and its image data is transferred to the computer 224. The computer 224 subtracts the image captured while the shutter unit 208 is closed from the fluorescent image of the biochemical examination array 100 that is captured while illumination light is applied in the same exposure time, thereby removing the dark noise generated by the CCD camera 220 itself. This noise removal processing may be performed within the CCD camera 220, and the resultant image may be transferred to the computer 224. This eliminates the necessity to perform transfer processing more than once and hence can further increase the processing speed.

Figure 6:
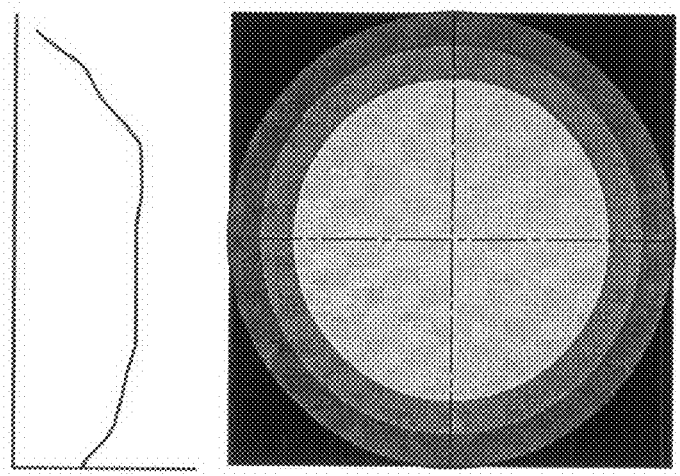
FIG. 6 shows that the intensity irregularity of illumination occurs from a central portion to a peripheral portion.
Figure 6:
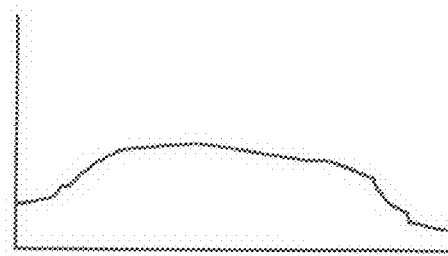

In general, as the camera captures a fluorescent image of the biochemical examination array 100 while prolonging the exposure time, intensity irregularity occurs from a central portion to a peripheral portion due to the influence of the aberration of the illumination optical system or the aberration of the observation optical system (the capturing optical system of the CCD camera in this embodiment), as is obvious from the change from FIG. 5D to FIG. 5E or from FIG. 6. For this reason, when the CCD camera 220 captures an image of a probe array element, a central portion of the resultant image and its peripheral portion have different intensity values even if the emission quantities of fluorescence are equal in these portions. This makes it impossible to perform accurate biochemical examination. So, the computer 224 calculates correction coefficients from the illumination intensity irregularity distribution of the biochemical examination array 100, and corrects the fluorescence emission intensities of all the probe array elements for each exposure time by using the calculated correction coefficients with respect to the images that have already been recorded (saved). In other words, the computer 224 constitutes correction means for correcting the fluorescence emission intensities of all the probe array elements for every exposure times by using correction coefficients calculated from an illumination intensity irregularity distribution with respect to the saved images.

In this embodiment, as an image for the calculating correction coefficients, the image transferred to the computer 224 immediately before the minimum value of pixel intensities in an area of a fluorescent image that is smaller than the entire area becomes greater than TransEnd is used. This is for calculating more accurate correction coefficients by effectively using the dynamic range of the CCD camera 220. The obtained fluorescent image of the biochemical examination array 100 is an image as shown in FIG. 5E, for example. Since probe array elements emit fluorescence, filter processing is applied to the image to erase the probe array elements by pixel interpolation to generate a correction coefficient calculation image as shown in FIG. 6. Correction coefficients are calculated from this correction coefficient calculation image.

The above series of operations allows capturing a fluorescent image of the biochemical examination array 100 without any problem. If, however, the examiner uses a wrong mixture of biochemical substance solutions or probe array elements are not properly generated, no correction binding reaction occurs in the biochemical examination array 100. As a result, the probe array elements may not emit fluorescence as expected. In this case, it requires a considerably long period of time to make the maximum intensity in the biochemical examination array 100 become greater than the pixel intensity indicated by TransStart. In this case, the experiment itself is a failure, and is a useless time-consuming operation because the examiner uselessly waits until the exposure time becomes considerably long.

In order to prevent such a situation, in this embodiment, when the exposure time becomes longer than MaxExpTime during repetitive image capturing, information indicating that a desired image could not be captured is displayed on the monitor 228, and image capturing is finished.

According to past experiences, it is often possible to estimate the required number of fluorescent images of the biochemical examination array 100 in consideration of the rate of increase in exposure time. In this case, waiting until the minimum value of the pixel intensities in an area of a fluorescent image that is smaller than the entire area becomes larger than TransEnd spends a useless time for examination.

For this reason, in this embodiment, when the number of fluorescent images becomes larger than the number indicated by TransPicts during repetitive image capturing, information indicating that the number of fluorescent images has reached the number indicated by TransPicts is displayed on the monitor 228, and image capturing is finished.

Figure 7:
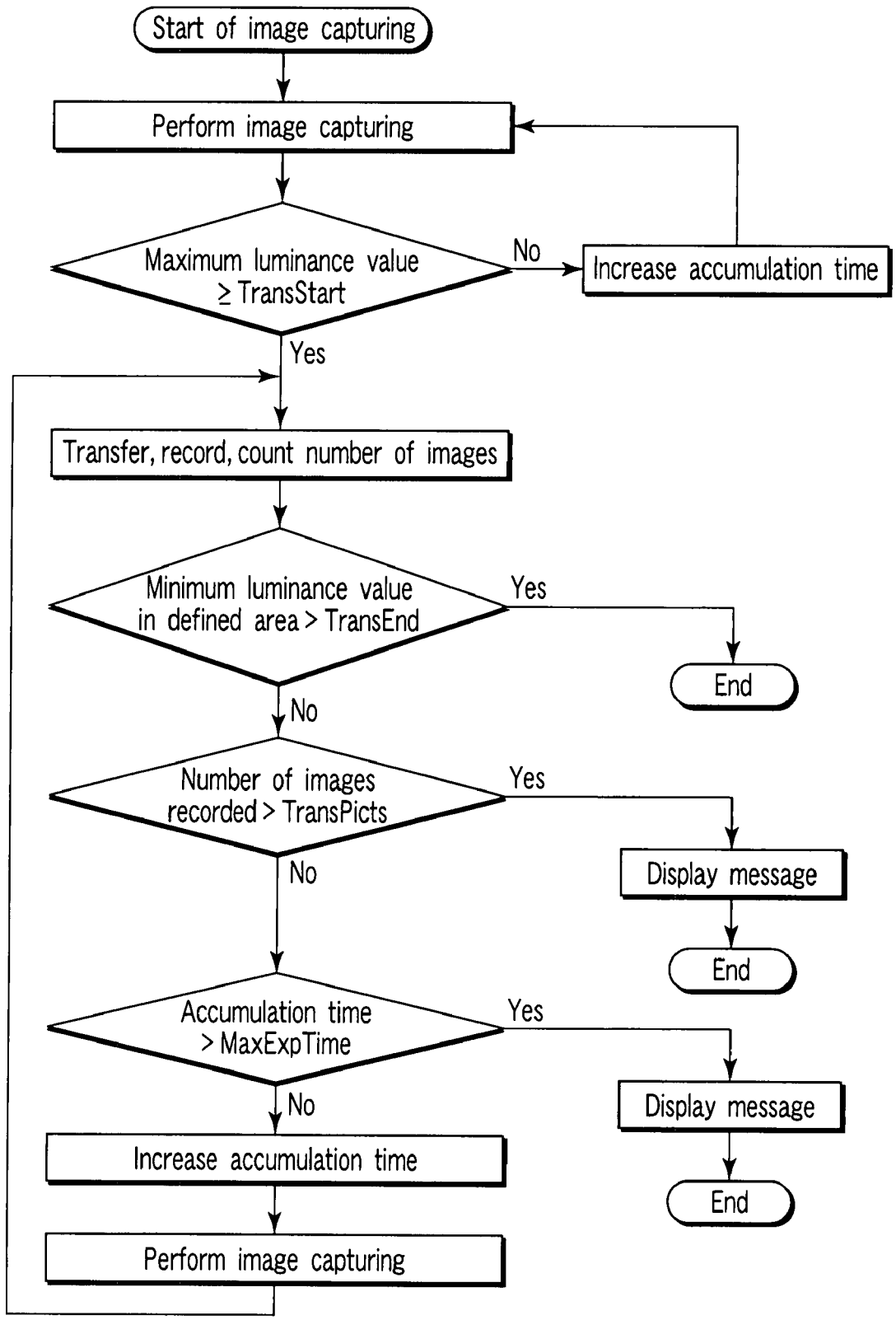
FIG. 7 shows a flowchart of the operation of the biochemical examination apparatus shown in FIG. 1.

FIG. 7 shows a flowchart for the above series of operations. As is obvious from FIG. 7, the following is a summary of the above series of operations. First, the camera captures a fluorescent image of the biochemical examination array 100 in the exposure time indicated by ExpStart. If the maximum intensity value of all the pixels of the fluorescent image is smaller than TransStart, the camera increases the exposure time and captures a fluorescent image of the biochemical examination array 100 again. After that, increase in the exposure time and capturing a fluorescent image of the biochemical examination array 100 are repeatedly performed until the maximum intensity value of all the pixels of the captured fluorescent image becomes equal to or greater than TransStart. When the maximum intensity value of all the pixels of the captured fluorescent image becomes equal to or greater than TransStart, image data is transferred to the computer 224 to be recorded (saved) on the hard disk in the computer 224, and the number of images recorded is counted. Subsequently, the increase in the exposure time, the image capturing, transfer and record of the image data, and count of the number of images recorded are repeatedly performed. The image capturing is finished when the minimum intensity value in an area of the fluorescent image that is smaller than the entire area becomes larger than TransEnd, the number of images recorded becomes larger than TransPicts, or the exposure time becomes longer than MaxExpTime.

The fluorescent image of the biochemical examination array 100 acquired by capturing, transferring, image processing in the above manner is divided by the computer 224 into portions for each probe array element and they are saved as divided images. At this time, the maximum intensity value of each probe array element area and the exposure time are added as data to a corresponding divided image. This operation is performed for all the exposure times. Finally, a hybrid image is formed. The hybrid image will be described with reference to FIGS. 8A to 8D.

FIGS. 8A, 8B, and 8C respectively show fluorescent images of the biochemical examination array 100 that are captured in exposure times of 400 ms, 800 ms, and 1,600 ms, respectively. On the fluorescent image in FIG. 8A, probe array elements A1 and A9 have intensity values as low as 200, and hence no light can be recognized. In the CCD camera 220 used in this embodiment, the intensity value range of 400 to 3,000 is regarded as the most linear and reliable range in consideration of the CCD and its peripheral circuit.

The computer 224 searches a plurality of recorded (saved) images for an intensity value equal to or less than 3,000 and nearest to 3,000 and the corresponding exposure time for each probe array element. More specifically, in the images shown in FIGS. 8A, 8B, and 8C, the intensity values of the respective probe array elements is detected and the data of an intensity value nearest to 3,000 from a plurality of intensity values (e.g., the intensity values of A1, B1, and C1) of the same probe and the data of the corresponding exposure time are extracted. Upon completing this operation for all the probe array elements, the intensity values of all the probe array elements are converted (normalized) into, for example, an exposure time of one sec, and the hybrid image shown in FIG. 8D is formed by combining the images of all the probe array elements after conversion. This image is displayed as a pseudo graphic image on the monitor 228.

The examiner examines the reaction degree of each probe array element on the basis of this pseudo graphic image and the converted data of each intensity value.

As is obvious from the above description, according to the biochemical examination apparatus of this embodiment, recorded (saved) fluorescent images of a biochemical examination array fall within a desired intensity range, so that any unnecessary images are prevented from being recorded (saved). In addition, defining a maximum exposure time and the number of fluorescent images to be acquired will prevent waste of time. So, an image of a biochemical examination array that has an optimal intensity for image analysis can be efficiently acquired.

This embodiment has exemplified the case wherein fluorescent dyes are used as label biochemical substances, and fluorescence generated by illuminating a biochemical examination array with a light source is acquired as an optical image. There are many kinds of fluorescent substances having various characteristics. So, it is preferable to use such substances because they allow a wide range of selection depending on applications. In addition to this, various detection methods and labels can be applied to the present invention. When chemiluminescence or bioluminescence is to be used, there is no need to use any light source for illuminating a biochemical examination array. If, for example, an enzyme is to be used as the label of a biochemical substance and is to be detected by a chemiluminescent method, since a reaction between the enzyme and the substrate generates light, there is no need to use any light source for illuminating a biochemical examination array. In this case, referring to FIG. 1, the universal control box 222, filter unit 212, lens 210, shutter unit 208, exciting light source 204, and power supply unit 206 are not always necessary.

In addition, when detection is to be performed with fluorescence, various kinds of fluorescent substances can be used as labels. A fluorescent glass particle, a fluorescent ceramic material, a fluorescent protein such as GFP, and the like can be used as well as fluorescent dyes. When detection is to be performed with scattered light or reflected light, a metal particle and a dielectric particle are used as labels. For example, a fine particle such as gold, silver, platinum, or silicon, a latex particle, and the like can be used. It is especially preferable to use a fine particle such as gold, silver, or platinum which has a particle size of 0.1 to 1 μm because the velocity of a particle in motion becomes an optimal velocity. An optimal particle size depends on the specific gravity and the velocity of the Brownian motion of the particle. Here, the motion state of the particle includes, for example, Brownian motion and oscillation.

As described above, when a biochemical substance is to be labeled and detected, the present invention can be applied to a case wherein not only fluorescent dyes but also other labels are used.

The embodiments of the present invention have been described with reference to the views of the drawing. However, the present invention is not limited to these embodiments, and various changes and modifications of the embodiments may be made within the spirit and scope of the invention.

For example, in the flowchart shown in FIG. 7, the processing of finishing image capturing when the exposure time becomes longer than MaxExpTime during repetitive image capturing may be omitted. Likewise, the processing of finishing image capturing when the number of images recorded exceeds the number indicated by TransPicts during repetitive image capturing may be also omitted.

This embodiment increases the exposure time in accordance with $10 \times 2^{n-1}$ [ms]. The present inventors have empirically confirmed that this manner of increasing the exposure time is especially effective. However, the manner of increasing the exposure time to be used is not limited to this. For example, the exposure time may be increased at a predetermined ratio (in a geometrical progression manner) or by a predetermined increment (in an arithmetical progression manner). Furthermore, the exposure time may be increased in accordance with a predetermined incremental pattern without any regularity between two consecutive exposure times.

The suitable rate at which the exposure time is to be increased depends on the characteristics of the camera (the dynamic range (the range in which outputs exhibit good linearity with respect to inputs), the photoelectric conversion efficiency, and the saturated electric charge per pixel) and the difference between the minimum and maximum values of signals to be acquired. That is, this rate varies depending on the camera to be used and the target to be detected. For this reason, it is preferable to determine this rate on the basis of the results obtained by repeated experiments.

As the rate of increase in exposure time decreases, the amount of information acquired increases. On the other hand, a longer period of time is required for processing. It is thus preferable to determine the rate of increase in exposure time in consideration of the tradeoff between the amount of information acquired and the time required for processing.

In addition, when examining similar samples and many reacted biochemical examination arrays, examination may be performed while optimizing the rate of increase in exposure time by feeding back examination conditions for every examination of a biochemical examination array. This effectively shortens the time required for processing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biochemical examination apparatus for measuring light emitted from a biochemical examination array to analyze a biochemical reaction, comprising:
    illumination means for applying exciting light to a biochemical examination array;
    capturing means for capturing an optical image emitted from the biochemical examination array; and
    recording means for saving the captured optical image;
    wherein the capturing means repeatedly captures an optical image while gradually prolonging an exposure time from an initial value defined by a first parameter;
    the recording means starts recording the optical image when a maximum intensity of all pixels of the captured optical image becomes equal to or greater than an intensity defined by a second parameter, and finishes recording an optical image when a minimum intensity of pixels in an area smaller than an entire area of the captured optical image becomes greater than an intensity defined by a third parameter; and the recording means finishes recording the optical image when the exposure time becomes larger than a value defined by a fourth parameter or the number of optical images recorded becomes larger than a value defined by a fifth parameter before the minimum intensity of pixels in the area of the captured optical image that is smaller than the entire area becomes greater than the intensity defined by the third parameter.

2. A biochemical examination apparatus according to claim 1, further comprising image forming means for forming a hybrid image from a plurality of optical images recorded on the recording means, wherein the image forming means divides the plurality of optical images saved in the recording means for each probe array element, selects a divided image having a suitable intensity value for each of the probe array elements, converts intensity values of all selected divided images into the same exposure time, and forms the hybrid image by combining divided images of all probe array elements after conversion.

3. A biochemical examination method for measuring light emitted from a biochemical examination array to analyze a biochemical reaction, comprising:
    applying exciting light to a biochemical examination array;
    repeatedly capturing an optical image emitted from the biochemical examination array in response to application of exciting light while gradually prolonging an exposure time from an initial value defined by a first parameter; and
    start recording the optical image when a maximum intensity of all pixels of the captured optical image becomes equal to or greater than an intensity defined by a second parameter during repetitive image capturing, and finishing recording the optical image when a minimum intensity of pixels in an area smaller than an entire area of the captured optical image becomes greater than an intensity defined by a third parameter; wherein recording of the optical image is finished when the exposure time becomes larger than a value defined by a fourth parameter or the number of optical images recorded becomes larger than a value defined by a fifth parameter before the minimum intensity of pixels in the area of the captured optical image that is smaller than the entire area becomes greater than the intensity defined by the third parameter.

4. A biochemical examination method according to claim 3, wherein a plurality of optical images saved in the recording means are divided for each probe array element, a divided image having a suitable intensity value is selected for each of the probe array elements, intensity values of all selected divided images are converted into the same exposure time, and a hybrid image is formed by combining divided images of all probe array elements after conversion.

* * * * *